United States Patent [19]
Angeles Uribe et al.

[11] Patent Number: 5,643,604
[45] Date of Patent: Jul. 1, 1997

[54] PARENTERAL DOSAGE FORM

[75] Inventors: Juan Angeles Uribe; Josué Garza Flores, both of Mexico, Mexico

[73] Assignee: Aplicaciones Farmaceuticas S.A. De C.V., Mexico

[21] Appl. No.: 94,579

[22] Filed: Jul. 14, 1993

Related U.S. Application Data

[63] Continuation of Ser. No. 714,630, Jun. 13, 1991, abandoned.

[30] Foreign Application Priority Data

Jun. 14, 1990 [FR] France ................... 90 07417

[51] Int. Cl.$^6$ .............................. A61K 9/10; A61K 9/16; A61K 31/565
[52] U.S. Cl. .................. 424/489; 264/13; 264/5; 514/177; 514/178; 514/182
[58] Field of Search ................. 424/489, 416, 424/422, 502, 484; 264/4, 5, 13; 514/169, 177, 178, 182

[56] References Cited

U.S. PATENT DOCUMENTS

| | | | |
|---|---|---|---|
| 3,691,090 | 9/1972 | Kitajima et al. | 427/213.36 |
| 3,773,519 | 11/1973 | Boswell et al. | 424/486 |
| 3,773,919 | 11/1973 | Boswell et al. | 424/486 |
| 3,937,668 | 2/1976 | Zolle | 264/4.3 |
| 3,982,537 | 9/1976 | Buscalo | 424/426 |
| 4,147,767 | 4/1979 | Yapel, Jr. | 424/489 X |
| 4,158,707 | 6/1979 | Steffen et al. | 514/221 |
| 4,244,949 | 1/1981 | Gupta | 514/178 |
| 4,331,654 | 5/1982 | Morris | 424/450 |
| 4,349,530 | 9/1982 | Royer | 424/489 X |
| 4,357,259 | 11/1982 | Senyei et al. | 264/4.3 |
| 4,384,975 | 5/1983 | Fong | 427/213.36 |
| 4,492,720 | 1/1985 | Mosier | 427/213.3 |
| 4,675,173 | 6/1987 | Widder et al. | 424/9.322 |
| 4,675,236 | 6/1987 | Ohkawara et al. | 428/402.24 |
| 4,711,783 | 12/1987 | Huc et al. | 424/460 |
| 4,745,907 | 5/1988 | Russel, Jr. et al. | 128/1.1 |
| 4,748,024 | 5/1988 | Leonard | 424/489 |
| 4,837,381 | 6/1989 | Steber et al. | 424/502 |
| 4,882,164 | 11/1989 | Ferro et al. | 424/450 |
| 4,892,734 | 1/1990 | Leonad | 424/422 |
| 4,963,367 | 10/1990 | Ecanow | 424/485 |
| 5,019,400 | 5/1991 | Gombotz et al. | 424/497 |
| 5,085,864 | 2/1992 | Cannon et al. | 424/450 |
| 5,360,616 | 11/1994 | Flores et al. | 424/489 |

FOREIGN PATENT DOCUMENTS

| | | |
|---|---|---|
| 0210875 | 4/1987 | European Pat. Off. . |
| 0257368 | 8/1987 | European Pat. Off. . |
| WO88/07816 | 10/1988 | WIPO . |

OTHER PUBLICATIONS

J. Garza Flores, et al., "Assessment of a New Low–Dose Once–A–Month Injectable Contraceptive," *Contraception*, vol. 35, No. 5, May (1988).

"Encyclopedia of Chemical Technology, Third Edition," vol. 15, John Wiley and Sons, pp. 470–493 (1981).

Institut national de la Propriete Industrielle, "Rapport de Recherche," (Search Report), French Patent Application 9007417, Feb. 2, (1991).

*Primary Examiner*—Melvyn I. Marquis
*Assistant Examiner*—Robert H. Harrison
*Attorney, Agent, or Firm*—Burns, Doane, Swecker & Mathis, L.L.P.

[57] ABSTRACT

Delayed-release formulation intended for administration by parenteral injection, consisting of solid calibrated microspheres (5–300 μm) comprising a pharmaceutically active substance (for example: morphine) contained in spherical structures determined by one or more which are pharmacologically inactive carrier substances (for example: cholesterol), naturally present in the receiving organism, which are pharmacodynamically inactive at the administered doses of said dosage form, having a melting point greater than 60° C. and stable in the solid state in the receiving physiological medium. The dosage form makes it possible to slow and prolong the effect of active substances which are too rapidly soluble in physiological medium (which act on the central nervous or neurovegetative system, such as vasedilators, anti-histaminics, hormones, contraceptives and the like).

21 Claims, 9 Drawing Sheets

PARTICLE SIZE DISTRIBUTION

PARENTERAL DOSAGE FORM

This application is a continuation of U.S. application Ser. No. 7/714,630, filed Jun. 13, 1991, now abandoned.

FIELD OF THE INVENTION

The present invention relates to a process for improving the control of the pharmacokinetic and pharmacological properties of an injectable pharmaceutically active substance, which is adaptable for parenteral administration by injection to a mammal or eventually to other animals. It furthermore relates to a solid and nonporous microsphere with a diameter of between 5 and 300 μm, comprising at least one pharmaceutically active substance contained in a spherical structure formed by at least one pharmacologically inactive carrier substance, said pharmaceutically active substance being capable of being administered by parenteral injection to a mammal, as well as to the use of such a microsphere for the manufacture of a formulation intended for parenteral administration by injection.

PRIOR ART

Biologically active substances which are weakly soluble in a physiological medium have already been used in the form of a suspension of particles and administered by intramuscular injection in order to obtain a slow dissolution and therefore a prolonged effect in the human or animal organism. For example, mixtures of norethisterone and mestranol, in the form of crystalline powder in aqueous suspension, have been tested with a view to manufacture of an intramuscular injectable contraceptive (J. Garza Flores et al., Contraception, May 1988, Vol. 35, No. 5,471–481).

Probably because of particle size variations and particle shape irregularities, these prior art compositions generally exhibit several defects:

Curve for the release of active substances exhibiting a sharp peak just after the injection and then a descending slope, which increases the total dose necessary to obtain an adequate, lasting effect.

Occasional formation of lumps or crusts in the suspension.

Necessity to use large diameter hypodermic needles in order to avoid the risk of a blockage in the syringe outlet.

For several substances, the direct contact of the active particle (very high local concentration) with the surrounding living tissue may cause inflammatory reactions or damages. Substances having a high solubility in physiological medium cannot be administered in this form if it is desired to obtain a "delayed effect". A known method for slowing the dissolution of such substances is to coat them or to microencapsulate them.

The Patent EP No. 257 368 (AMERICAN CYANAMID CO) describes a composition for parenteral use consisting of microspheres of fats and/or waxes, of natural or synthetic origin, of low melting point (40° to about 60° C.) and loaded with particles of a polypeptide, for example a growth hormone. When these compositions are injected into cattle, the dissolution of the growth hormone is delayed by wax or fat coating, which prolongs its presence in the animal organism, causing an increase in growth or in lactation. These microspheres have a tendency to soften and to deform, to agglutinate or to coalesce when the ambient temperature is high, particularly in tropical countries (40°–60° C.), which may cause handling or storage problems.

As the proportion of active polypeptide in the particle is limited in practice to 30–40%, the injection of these particles also has the disadvantage of introducing in the organism a quantity of carrier substance which is foreign to this organism (beeswax, fat of plant, mineral or synthetic origin, and the like), and which is at least of the order of 1.5–3 times that of the active substance. Other coating or microencapsulation techniques have been used in the prior art, some of which are described, for example, in "Encyclopedia of Chemical Technology, 3rd edition, volume 15, pages 470 to 493 (1981), JOHN WILEY AND SONS. The microcapsules thus formed often contain "central" particles of very different sizes, or even no central particle at all.

The Patent EP No. 210 875 (TERAGENIX CORP.) describes the injection of radioactively charged glass microbeads into a body, for example into the liver, for the local treatment of a cancerous tumor. The persistence of such beads after treatment is justified only in serious cases. The elimination of the carrier substance by the metabolic pathways of the internal medium may be difficult; such a substance is acceptable for oral administration (and elimination through the digestive tracts) in human medicine, but much less so for parenteral injection in human medicine.

Moreover, steroid hormones have been used as means of contraception in the form of subcutaneous implants. These implants, of 0.5 to 2 cm in length, may be manufactured by melting and shaping of the hormone in the melted state, pure or mixed with a lipoid carrier. These manufacturing processes are described for example in WO-88/07816 (Endocon) or in the U.S. Pat. No. 4,244,949 (Gupta). The duration of action of these implants may exceed one year; in contrast, this system is unsuitable when the desired durations of action are a few weeks only. Said system needs to be put in place by surgical incision or by trocar, and to be removed by excision, if appropriate.

SUMMARY OF THE INVENTION

The aim of the present invention is to provide delayed-release formulations for administration by parenteral injection, through a needle, to man or other mammalians, which permits a controlled release of the pharmacologically active substances without exhibiting the disadvantages of the particle or microcapsule suspensions of the prior art.

This aim is achieved by virtue of a process consisting in preparing said substance in the form of solid, nonporous microspheres of a diameter of between 5 and 300 microns, comprising at least one pharmaceutically active substance contained in a spherical structure formed by at least one pharmacologically inactive carrier substance, said carrier substance forming the spherical structure being naturally present in the body of said mammal and being stable in the solid state up to a temperature of at least 60° C. and in the physiological medium of said mammal, the kinetics of dissolution of the carrier substance in the receiving mammalian organism being slower than the kinetics of release of the active substance in this same organism, and in separating said microspheres into calibrated fractions according to their diameters, and by virtue of their use for the manufacture of a formulation intended for parenteral administration by injection.

By stable in the solid state up to 60° C., it should be understood that not only do the microspheres not melt, but also they do not soften and do not agglutinate.

By stable in the solid state, within the meaning of the present invention, there should also not be understood the indefinite stability which a glass microsphere would have for example, but sufficiently stable for the order of magnitude of the period of stability in this medium (the disappearance of the spheres occurring by simple slow dissolution or by metabolic chemical attack) not to be lower than the desired duration of action of the medicinal product: in other words, the kinetics of dissolution of the carrier substance in the body of the receiving mammal should be slower than the kinetics of release of the active substance in this same organism.

If a spraying/freezing process is used for the manufacture of the microspheres, the carrier substance should be chemically stable at its melting temperature and in the melted state in at least one temperature region which is adequate for this operation.

The rate of dissolution of a microsphere in a given solvent medium is a function of the radius of the sphere (taking into consideration the relationships between volume, surface area and radius of a sphere). According to one aspect of the present invention, the use of solid, non porous spheres makes it possible to have precise knowledge of the mass-surface area relationship of the particles and therefore, by virtue of a selection of the size of the spheres, that is to say of the radius or of a distribution of radii, to regulate a control parameter of the rate of release of the active ingredient or active ingredients administered.

The rate of dissolution of the active ingredients also depends on the structure of the microsphere, and in particular on the accessibility of its inside to the solvent. An inactive substance which for example acquires the structure of a swollen gel in physiological medium (for example a collagen fraction) produces only a small delay in the release of active substances, whereas a substance with a compact hydrophobic structure provides a maximum-delay effect. According to another aspect of the present invention, the selection of the molecule which determines and structures the microsphere makes it possible to obtain a delayed release of the active ingredients which varies from a few hours to several weeks.

If the pharmacologically active substance is in the form of a solid solution (for ex.eutectic) in the carrier substance or of a virtually homogeneous suspension of dispersed particles which are small (for ex. colloids) relative to the diameter of the microsphere (10–300 µm), its dissolution is slowed, depending upon the concentrations.

If the active substance is in the form of larger particles coated in an external layer of hydrophobic substance, the onset of dissolution is delayed. For technical reasons relative to the manufacturing process, the size of the coated particles is limited relative to the diameter of the microspheres: in the spraying/ freezing process, it is preferable to limit the size of the particles to 1/10 of that of the microspheres.

The adjustment of these various parameters permits, according to the invention, precise control of the release of the active ingredients. This same precision of control, by avoiding overdosages or the need to compensate for underdosages, makes it possible to reduce the total quantity, which is envisaged for administration, of the biologically active substance or substances to the minimum quantity required in order to obtain the desired therapeutic effect and to thereby reduce the risk of producing undesirable side effects in the patient.

An injectable dose of 200 mg of microspheres per ampoule containing up to 50 mg of active ingredient can be considered to be reasonable.

Some additive substances in the combination may be not directly active on the receiving organism, at least in the intended application, or constitute the basis of the spherical structure. The combination may comprise various pharmaceutically acceptable means for improving the stability or the chemical integrity of the substances or of the overall structure: surfactants, antioxidants, antimicrobial agent, buffer and the like. In particular, it may be useful to reduce the melting point or inhibit a decomposition reaction during the microsphere manufacturing process (for example melting/freezing).

Relative to suspensions of pure active ingredients in the form of particles of irregular shapes known in the prior art, the microspheres according to the present invention have the advantage of possessing a lesser tendency to agglutinate and of passing more fluidly through a hypodermic needle. On the other hand microspheres may be more accurately and more easily separated, fractionated and calibrated according to their size then particles of irregular shape can be.

The dosage form according to the present invention may take the form of a microsphere powder in vials/ampoules, ready to be prepared as suspensions, or take the form of ready-prepared suspensions, packaged into injectable ampoules or directly into syringes, ready to be administered in human or veterinary medicine. The suspension medium may be water, a saline solution, an oil, containing buffers, surfactants, preservatives, commonly used by pharmacotechnicians for preparing injectable substances or any other substance or combination which does not threaten the physical and chemical integrity of the substances in suspension and which is suitable for the organism which will receive it. If it is desired to avoid a sudden initial increase in the level of active ingredient in the internal medium of the receiving organism, it will be preferable in the case of ready-for-use suspensions to use liquid vectors in which said active ingredients are practically insoluble. In the case of active substances partially soluble in the lukewarm liquid vector but insoluble at cold temperature, it is preferable, from the pharmacological point of view, to avoid the formation of precipitates (called "caking" effect) by preparing formulations in the form of separate microsphere powder and liquid vector which will be mixed only at the time of injection.

In veterinary applications, where the duration of the desired effect may be very long (for example the lactation period of the adult female), diameters of a few hundreds of microns may be used. If it is desired to limit the diameter of injection syringe needles for the comfort of the patient, the diameter of the microspheres should be limited to 300 microns and more preferably to 100 microns. In contrast, for very short durations of effect (for example circadians), the diameter of a microsphere may be reduced to 5 microns.

For most applications in human medicine (duration of action of the active ingredient between a circadian cycle and a menstrual cycle), it is preferable to use microspheres whose diameter is between 5 and 100 microns, depending on the combinations of active substances/carrier substances.

A separation of microspheres according to their diameter may be performed during the manufacturing process using known processes: for example, by cyclonic separators, by sieving using air suction or by sieving in aqueous medium. In practice, it is sufficient if more than 70% of the microspheres have diameters of between 70% and 130% of a specified diameter. If necessary, the ideal dissolution curve, determined by the proposed application, may be approached by mixing batches with suitable different diameters. Moreover, particles which do not comply with the specifications may be recycled.

Processes for preparing a solid product in the form of microspheres by mechanical abrasion are known in the state of the art. Other processes use, for example, the suspension of the product in the melted state in the form of microdrops, with stirring, in a liquid vector with which said product is non-miscible, followed by solidification of said product. In order to achieve the microspheres according to the present invention, it was preferred to develop a process which consists in spraying under pressure and/or using a hot gas (with optional vibrations) the substance intended to constitute the spheres, in the melted state, in which the pharmacologically active substances are either in the dissolved state or in the form of particles <5 μm, and therein rapidly freezing the cloud thus formed. Nevertheless, it is difficult to make microspheres of less than 2 μm diameter, bearing solid coated particles, by means of a spray-freezing process.

Pharmacodynamically inactive substances according to the invention whose melting temperature is greater than approximately 70° C. and which are or may be made thermostable above their melting point so as to be able to undergo the manufacturing process make it possible to achieve stable microspheres (no softening or agglutination) at low or average ambient temperatures.

However, insofar as the active ingredient in suspension tolerates high temperatures without decomposition or melting/separation, it is preferable, in order to avoid a risk of modifying the microspheres during an accidental large rise in temperature (transportation, storage), to choose a carrier substance whose melting temperature is greater than 90° C. to constitute the structure of the microsphere.

Among the preferred carrier substances, there may be mentioned by way of inactive substances which can constitute the structure of the microspheres: 1. Coprosterol, of melting point 101° C., which is a product obtained by metabolization of sterols and which participates in the formation of steroids and bile acids. 2. Glycocholic acid, of melting point 130° C., which is a member of the bile salts. 3. Cholesterol, of melting point 148°–149° C., principal sterol in mammals, present in practically all the tissues of the human organism, and its esters.

It may appear surprising to inject suspensions of cholesterol particles to a human being, considering the part which is attributed to this substance in several cardiovascular diseases. But, compared to the 8–10 gms naturally present in the free state in the physiological medium, the 50–200 mg of an injection are of a small entity. Moreover its relatively slow metabolism leads to consider this substance as pharmacodynamically inactive at these injected doses. On the other hand its physical properties are excellent for a carrier substance, in the frame of the present invention.

The pharmacologically active substances which are particularly suitable for this dosage system are those which 1/are soluble (or reactive) in biological fluids, 2/ which, although tending to decompose at very high temperatures close to or greater than their melting point, remain physically and chemically stable at the melting point of the inactive structural substance.

An example is methoclopramide, an anti-emetic freely soluble in water.

Another example is morphine basic, a narcotic analgesic, whose melting point is 254°–256° C., and which becomes physically and chemically unstable towards 200° C. The morphine (particles of the order of 1 μm to 5 μm, or smaller) is dispersed in liquid cholesterol (mp=148° C.) without risk of decomposition. The mixture is sprayed and frozen into microspheres. In this form, morphine may for example be administered as a daily injection, in a hospital environment, of 50 mg of morphine contained in 200 mg of microspheres/ampoule (highly variable dose because of the individual reactions to morphine); for an outpatient, it will be preferable to adapt the presentation (dose and structure of the spheres) for an injection every 2–3 days, or weekly.

Among the active substances which are too soluble in physiological medium in order to be administered in the free state while presenting a delay-effect, and which are sufficiently stable at high temperature in order to be incorporated into cholesterol, the following may be mentioned in particular:

a) substances which act on the central nervous system (tranquilizers such as LORAZEPAM, HALOPERIDOL, anti-parkinsonians such as BIPERIDEN, TRIHEXYLPHENIDYL HCL, anticonvulsants such as CLONAZEPAM, narcotics such as MORPHINE BASE)

b) substances which act on the neurovegetative system (anti-emetics such as METHOCLOPRAMIDE, ACEPROMAZINE MALEATE, gastrokinetic drugs such as DOMPERIDONA)

c) peripheral vasodilators such as VINCAMINE, NYLIDRIN HCL, FLUNARIZINE, PIZOTIFEN, DIHYDROERGOTAMINE, or bronchitic drugs such as BROMOHYDRATE, FENOTEROL, TOLBUTEROL, CLENBUTEROL and SALBUTAMOL d) antihistaminics (ASTEMIZOLE, CHLORFENAMINE MALEATE and AZATADINE)

e) $H_2$ receptor antagonists, FAMOTIDINE f) several steroids (DEXAMETHASONE, BETAMETHASONE) are also suitable.

The dissolution of several analgesics, even poorly and slowly soluble in water, like indomethacin or naproxen, may be even more slowed down and delayed by incorporating these substances in a cholesterol structure (this allows to space the times of injection, inasmuch as the unit dose are increased). The present invention will be better understood by means of the illustrative figures and examples. It is however not limited to these embodiments.

EXAMPLE 1

Manufacture of cholesterol microspheres.

Figure 1:
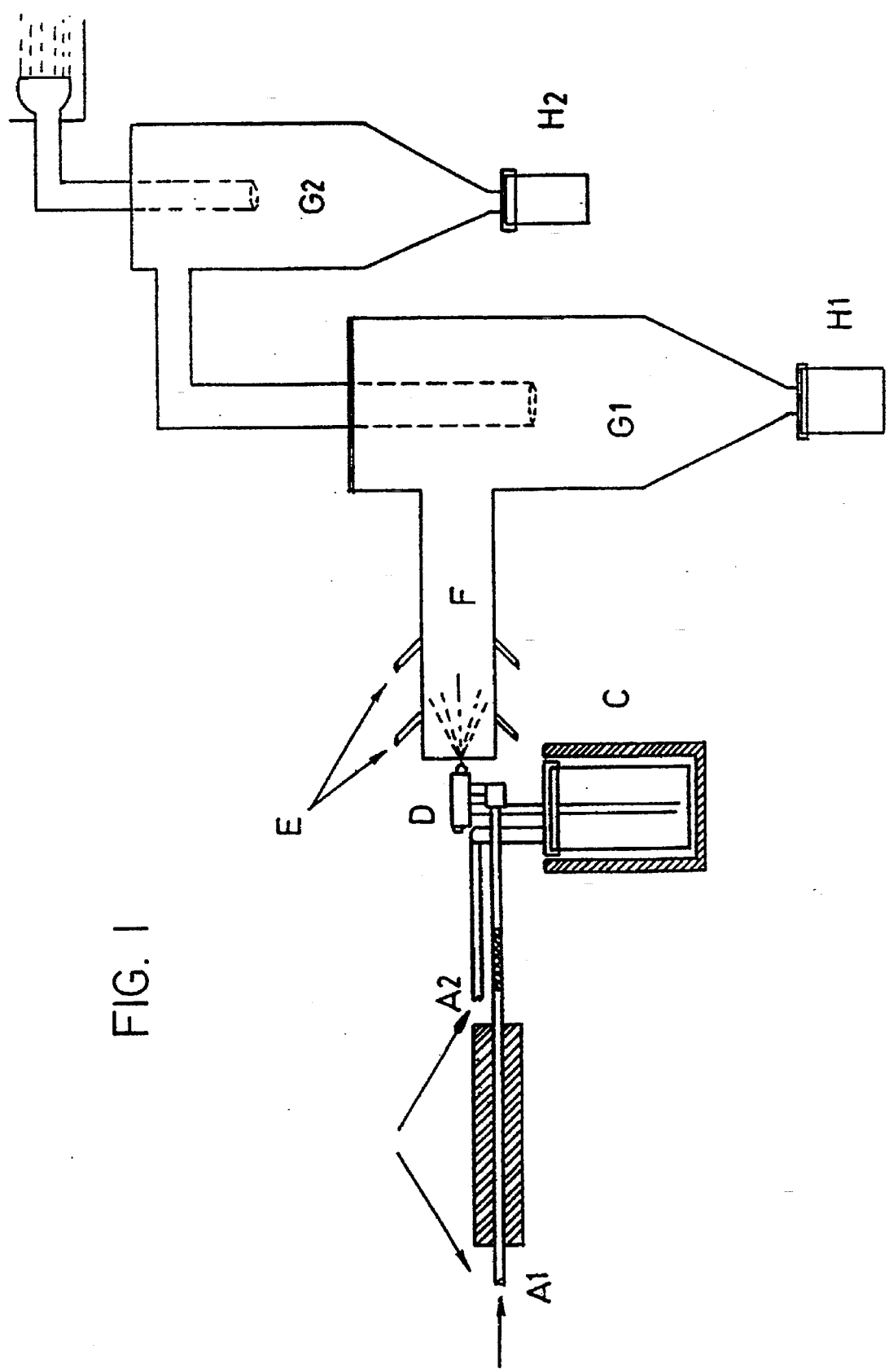
FIG. 1 shows a diagram of the manufacture of cholesterol microspheres according to the present invention.
Figure 2:
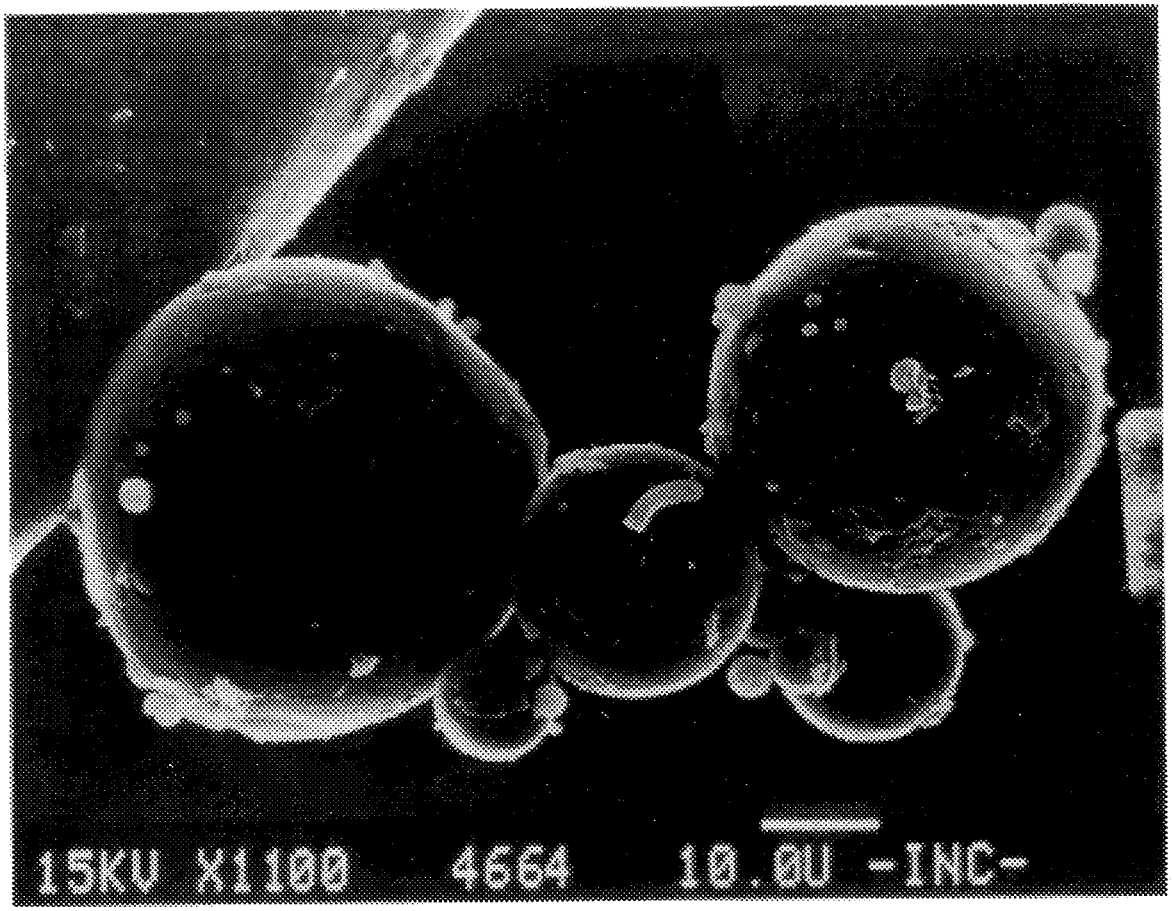
FIG. 2 shows a microphootograph (electron microscope) of cholesterol microspheres.

We refer to FIG. 1. Preheated nitrogen under pressure is fed by the inlet tube $A_1$ into the spray device and crosses a thermoregulated heating zone B, where it is brought to a temperature of between 160° and 190° C. before being admitted into the sprayer D. The sprayer D is connected by a pipe to a heated chamber C in which the cholesterol is maintained in the melted state (mp=148° C.) and under nitrogen pressure (inlet $A_2$). It is carried by the nitrogen current and mixed with the latter in order to be sprayed into a cloud by the outlet nozzle of the sprayer D and penetrates into the spraying/freezing chamber F. A reservoir E contains liquid nitrogen which evaporates and penetrates via several tubings in the form of ultra-cold gas, at high speed, into the spraying/freezing chamber F, where it meets the cholesterol cloud. Immediately after their formation by the sprayer, the droplets are surrounded by a current of ice-cold gas which crystallizes them into microspheres and prevents them from touching the side walls before their complete solidification. The temperature at the outlet of the spraying/freezing chamber is between −15° C. and −50° C. All the microspheres produced by means of this chamber F have a perfect spherical shape. At the outlet of this chamber F are two cyclonic separators $G_1$ and $G_2$ (of known construction moreover) mounted in series. The microspheres are recovered in collecting vessels $H_1$ and $H_2$; at the outlet of the cyclones, the gases pass through a decontaminating filter I in which a slight vacuum, relative to the pressure prevailing in the first cyclone, is maintained by means of a pump. FIG. 2 shows a fraction of recovered cholesterol microspheres using microphotography (electron microscope).

EXAMPLE 2

Particle size distribution

The cholesterol microspheres, manufactured under the operating conditions above, are separated into fractions.

Figure 3:
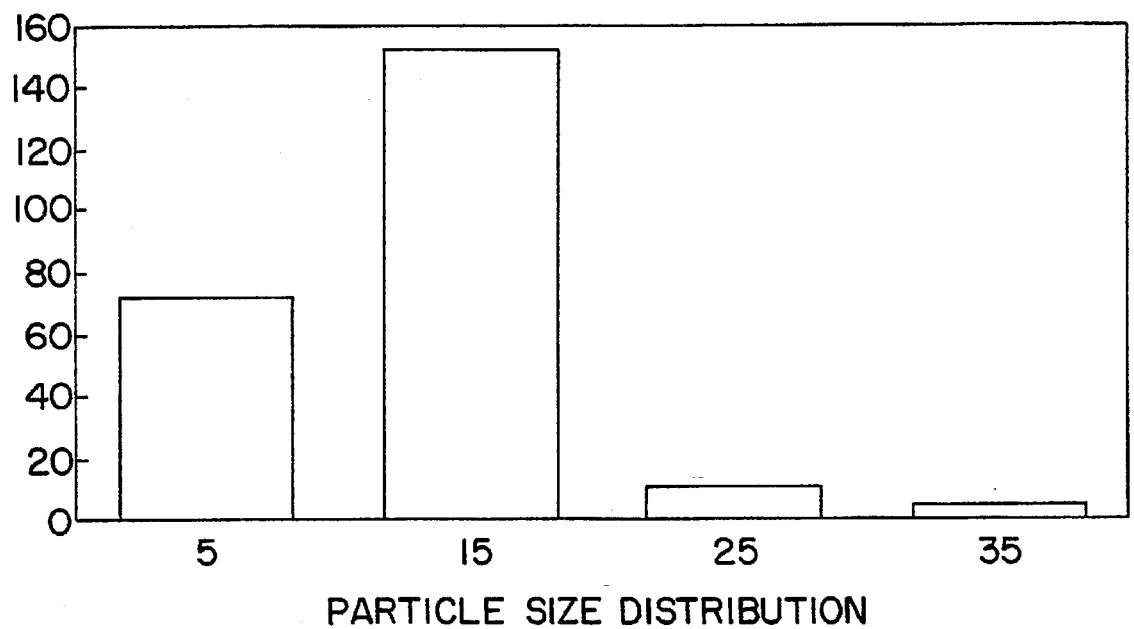
FIG. 3 shows the particle size distribution of a cholesterol microsphere fraction (mean diameter 15 μm)
Figure 4:
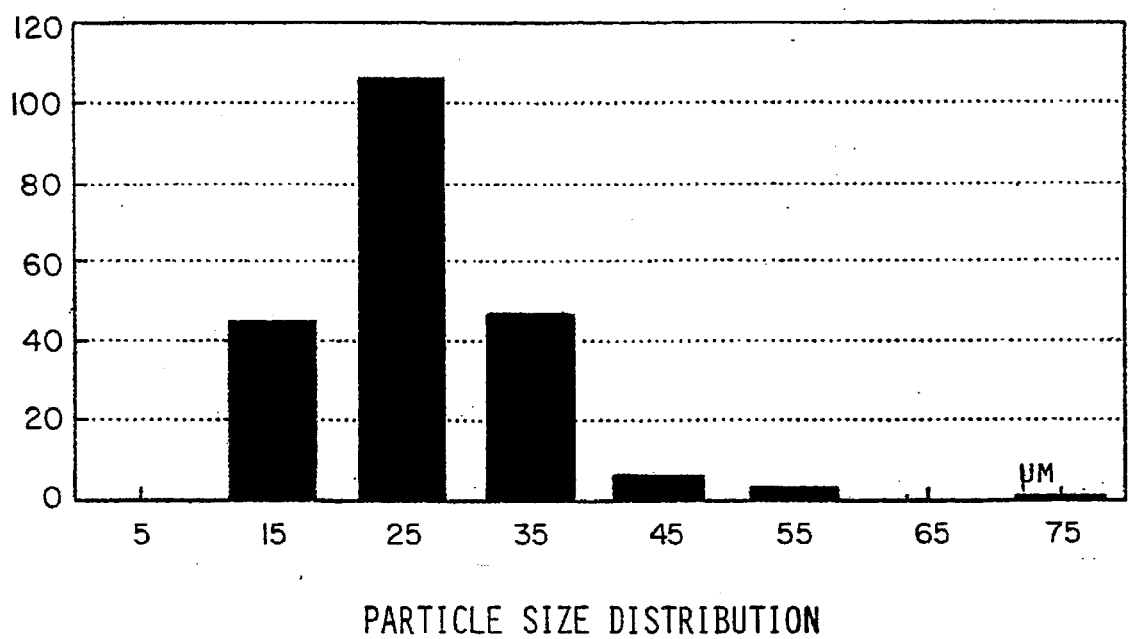
FIG. 4 shows the particle size distribution of a cholesterol microsphere fraction (mean diameter 25 μm)

FIGS. 3 and 4 show the particle size distributions of fractions centered around 15 m and 25 m respectively.

EXAMPLE 3

Manufacture of 17-β-estradiol/cholesterol microspheres.

The process in Example 1 is applied to a 17-β-estradiol/cholesterol mixture in a weight ratio of 1/9.

Operating conditions:

Melting : 149° C. in nitrogen atmosphere.

Sprinkling: by valve, with air pressure of 2,5 psi (200 gr/cm$^2$)

Freezing : by air at −20° C., under pressure of 4 Kg/cm$^2$

Recovery : by cyclones

Selection : in aqueous medium and by screening according to particle size.

EXAMPLE 4

Manufacture of diazepam/cholesterol microspheres.

The process in Example 1 is applied to a diazepam/cholesterol mixture in a weight ratio of 1/2.

Operating conditions:

Melting : 138° C. in nitrogen atmosphere

Sprinkling : by valve, with air pressure of 1,5 psi (100 gr/cm$^2$)

Freezing : by air at −20° C., under pressure of 4kg/cm$^2$

Recovery : by cyclones

Selection : in aqueous medium and by screening according to particle size.

EXAMPLE 5

Manufacture of caffeine/cholesterol microspheres. The process in Example 1 is applied to a caffeine/cholesterol mixture in a weight ratio of 1/2.

Operating conditions:

Melting : 165° C. in nitrogen atmosphere

Sprinkling : by valve, with air pressure of 2 psi (140 gr/cm$^2$)

Freezing : by air at −20° C., under pressure of 4 kg/cm$^2$

Recovery : by cyclones

Selection : in aqueous medium and by screening according to particle size.

Comparative UV and IR Spectrophotometric analysis before and after formation of microspheres.

It is necessary to check that no chemical damage of the substances occurs during the spray-freezing process, which could modify their therapeutic properties. The starting materials (crystals) and the microspheres obtained by spray-freezing are compared by UV and IR spectrophotometry. UV spectras shall always be superimposable and IR spectras shall correspond. If differences in infrared spectras appear, it shall be checked if they are due to a polymorphism phenomenon, by means of an HPLC setup with diode-array detection. Differential thermal analysis is also used, not only to check the melting points, but also to determine if endothermic or exothermic transitions occur, due either to structure modifications or to a polymorphism, which may influence the microsphere information process, or due to heat-induced chemical reactions.

Equipment used in ultraviolet spectrography: Hewlett Packard model 8452A with photodiode arrangement and quartz cell with a beam of 0.1 cm. Solvents: ethanol for 17-beta-estradiol and cholesterol; 0.1N HCl for diazepam, butylhioscine bromide and caffeine. The results show no trace of modification.

Equipment used in infrared spectrophotometry: Nicolet 205 FT-IR. Dispersion medium: potassium bromide. Chromatography: HPLC device with photo diode-array detector, model Waters 990 and Nec powermate 2 workstation. The results show no modification after the formation of microspheres of cholesterol, 17-beta-estradiol and diazepam. In contrast, it appears that for butylhioscine bromide, microferulization produces chemical modifications.

Thermal analysis: Shimadzu DSC 50 calorimeter and CR4A workstation. On the differencial thermograms, no degradation of 17-beta-estradiol, diazepam and caffeine appears.

Figure 5:
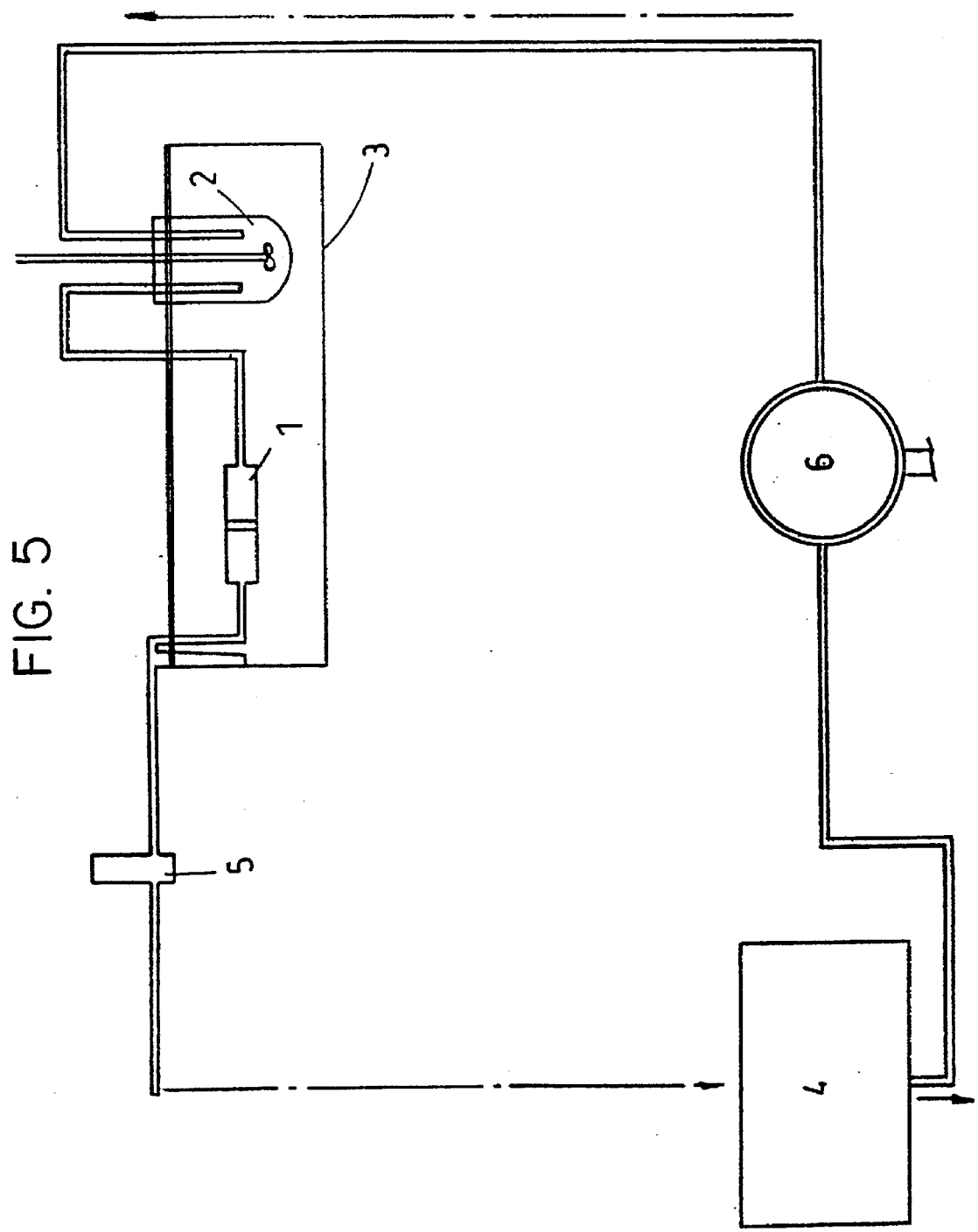
FIG. 5 represents an experimental setup for determining the rate of dissolution of microspheres.

The experimental setup for the in vitro dissolution tests is shown in FIG. 5. An infusion cell 1, containing the sample, is fed by a reservoir (stirred) of dissolution medium 2; both are kept on a water bath 3. The optical density of the medium is recorded by a spectrophotometer 4 and the medium is returned into the reservoir. A bubble trap 5 and a peristaltic pump 6 complete the circuit.

The following examples show the Comparative reproducibility of the initial parts of the dissolution curves of crystals and microspheres of comparable size, for the same product. Several (3–6) measurement circuits (dissolution cells and tubings) containing identical samples are processed in parallel by the same peristatic pump and measured simultaneously.

EXAMPLE 6

Dissolution of 17-beta-estradiol/cholesterol microspheres:

The equipment used is that in FIG. No. 5

Dissolution medium used: $H_2O$ HPLC quality with 0.01% of Tween 80

Sample: 50 mg

Particle size: 50 to 100 microns

Sampling intervals: 0, 3, 6, 9, 12, 24 hours

Spectrophotometric wavelength: 282 nm

Figure 6:
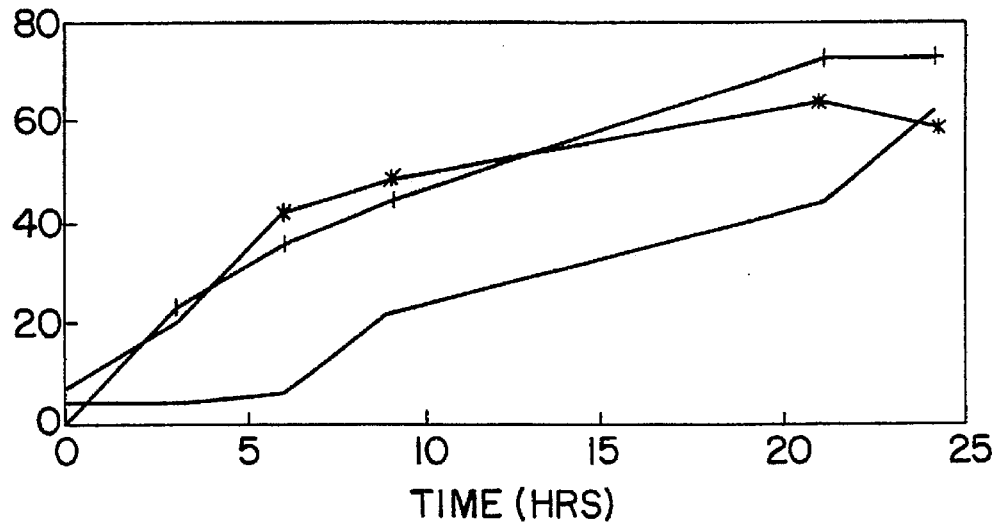
FIGS. 6 and 7 show the dissolution profile of microspheres (FIG. 6) of 17-β-estradiol carried by cholesterol, compared with the dissolution profile of 17-β-estradiol crystals (FIG. 7).
Figure 7:
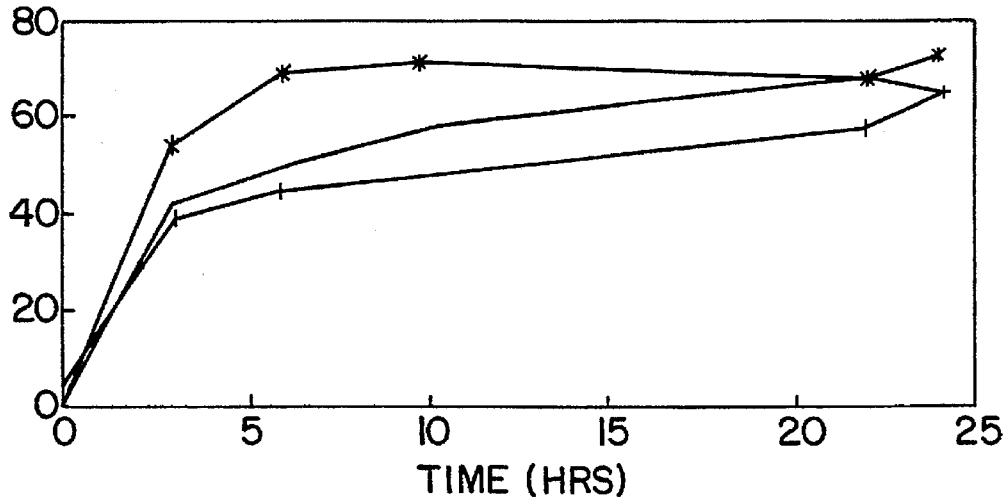

The dissolution curves of microspheres are shown in FIG. 6. It may be compared to the dissolution curve of a material constituted by the same starting components, melted, cooled down, crashed and mechanically micronized (FIG. 7).

EXAMPLE 7

Dissolution of diazepam/cholesterol (1/2)

Dissolution medium used: $H_2O$ HPLC quality with 0.01% of Tween 80

Sample: 50 mg

Particle size: 50 to 100 microns

Sampling intervals: 0, 1, 2, 4, 8 hours

Spectrophotometric wavelength: 286 nm

Figure 8:
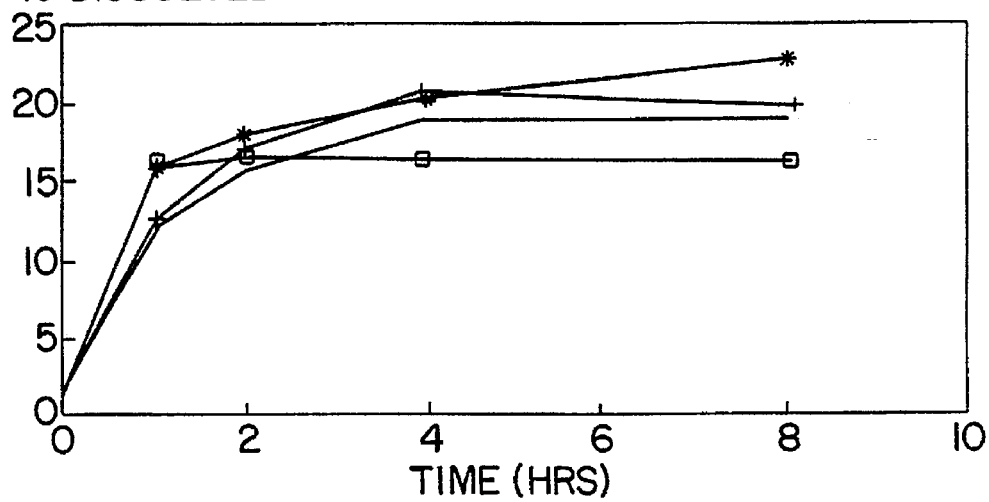
FIGS. 8 and 9 show the dissolution profile of microspheres of (FIG. 8) diazepam carried by cholesterol, compared with the dissolution profile of diazepam crystals (FIG. 9)
Figure 9:
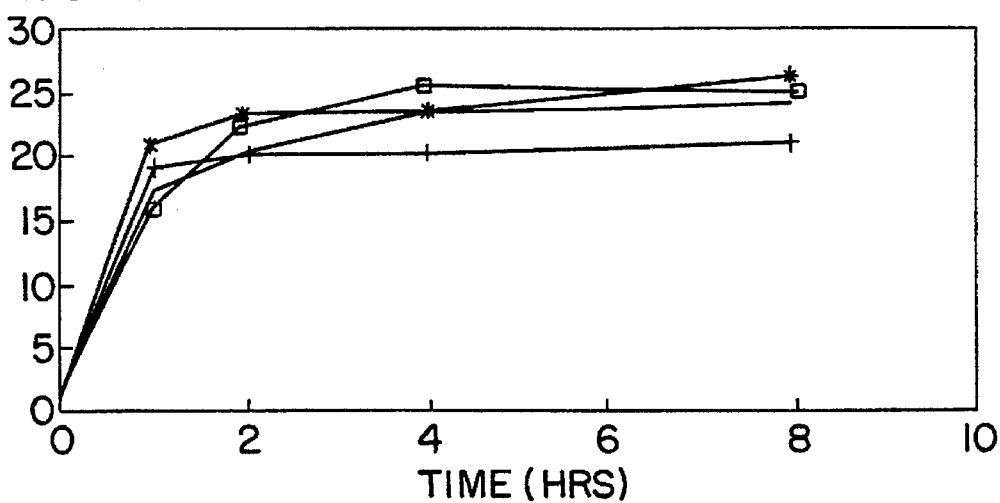

The dissolution curves of microspheres are shown in FIG. 8 whereas the dissolution curve of micronized crystals is shown in FIG. 9.

EXAMPLE 8

Dissolution of butylhioscine bromide/cholesterol (1/4) microspheres: The equipment used is that in FIG. No. 5

Dissolution medium used: $H_2O$ HPLC quality with 0.01% of Tween 80

Sample: 50 mg

Particle size: 50 to 100 microns

Sampling intervals: 0, 1, 2, 4, 8 hours

Spectrophotometric wavelength: 284 nm

The dissolution curves, not shown here, are closely similar to the preceding ones.

EXAMPLE 9

FORMULATIONS

| Formula No. 1 | |
|---|---|
| 17-beta-estradiol/cholesterol* microspheres | 25 mg |
| Polyethylene glycol 800 | 20 mg |
| Carboxymethylcellulose sodium | 1.66 mg |
| Polysorbate 80 | 2.0 mg |
| Propylparabene | 0.14 mg |
| NaCl | 1.2 mg |
| $H_2O$ cbp | 1 ml |

*equivalent to 2.5 mg of 17-beta-estradiol

| Formula No. 2 | |
|---|---|
| Diazepam/cholesterol microspheres 33% | 33.3 mg |
| Polyethylene glycol 4000 | 3.0 mg |
| NaCl | 8.5 mg |
| Benzyl alcohol | 9.0 mg |
| Sodium hydroxide or HCl: | sufficient for pH 5–6 |
| $H_2O$ cbp | 1 ml |

*Equivalent to 10 mg of diazepam.

EXAMPLE 10

STUDY OF THE PLASMA LEVELS OF 17-BETA-ESTRADIOL/CHOLESTEROL IN RABBITS

Figure 11:
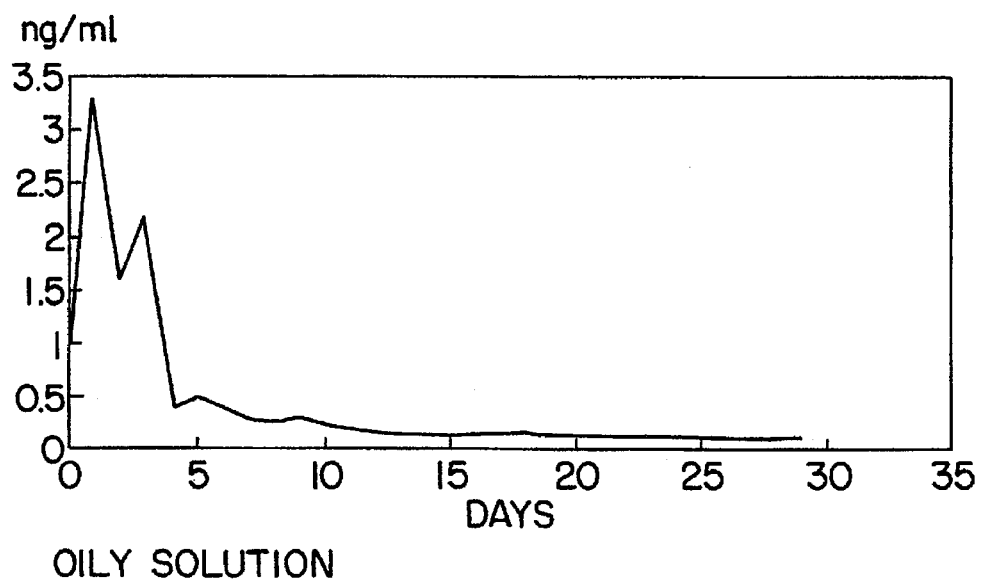
FIGS. 11, 12, 13 show the plasma levels of 17-β-estradiol obtained in rabbits by injection of a solution (curve 0) of a micronized material mixture estradiol/cholesterol (curve 1) and of microspheres of estradiol/cholesterol (curve 2) respectively.
Figure 12:
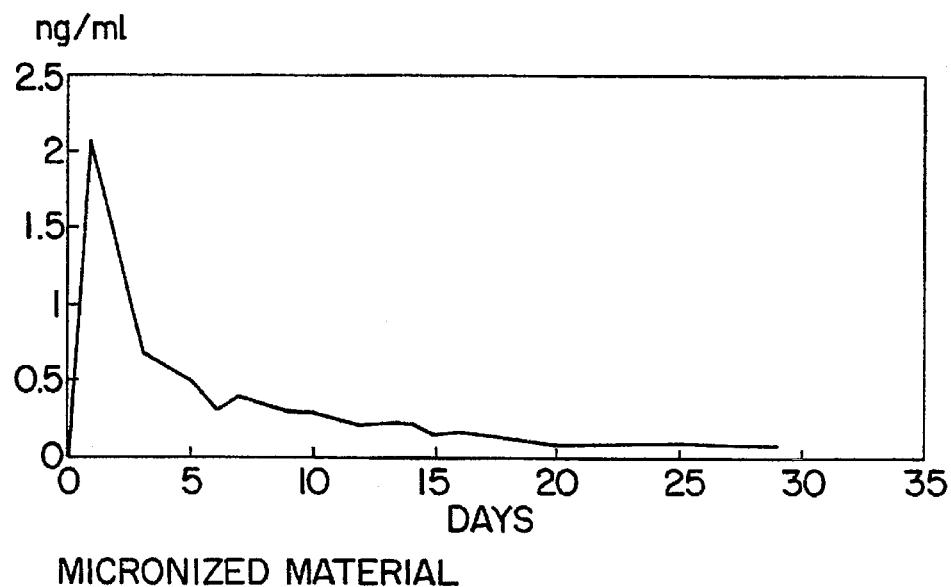
Figure 13:
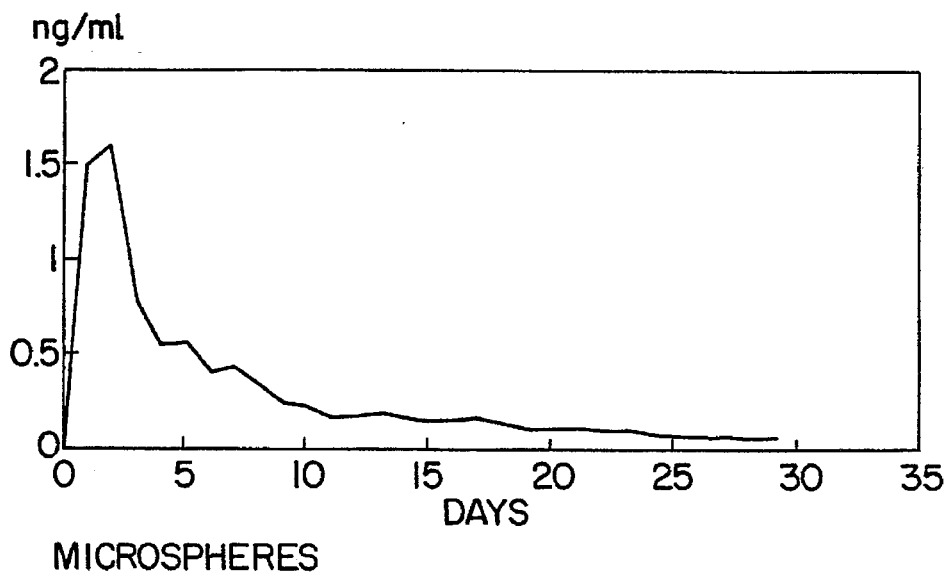

The study comprises the comparative evaluation of the effect on the plasma levels in rabbits produced by the parenteral administration of estradiol in the form of an oily solution (FIG. 11), and aqueous suspension of estradiol/cholesterol particles (FIG. 12) and an aqueous suspension of estradiol/cholestero microspheres (FIG. 13), according to Formula No. 3.

A single intramuscular dose of 5 mg of estradiol is administered to 10 male rabbits of New Zealand breed having an average weight of 3.5 kg.

The sampling interval is 1,2,4 and 24 hours for 20 days and then every three days up to 30 days.

2-ml samples are taken by venopuncture and are centrifuged and kept at 20° C. until their analysis by radioimmunoassay.

EXAMPLE 11

COMPARATIVE EVOLUTION OF THE PLASMA LEVELS OF DIAZEPAM IN OILY SOLUTION AND IN MICROSPHERE SUSPENSION (Formula No 2)

Experimental animals: rabbits of New Zealand breed aged about 5 months and weighing on average 3.7 kg.

The reference sample is 5 ml of blood taken by cardiac puncture, followed by the intramuscular administration of 2 ml of the test formula into the lower right leg.

The analytical samples were taken at intervals of 30 min for 2 hours and at intervals of 60 min up to the end of 6 hours. In some cases, depending on the kinetic characteristics of the medicinal product, additional samples were taken.

2-ml analytical samples, also taken by cardiac puncture, were placed in a Vacutainer, heparin was added and the mixture was centrifuged at 3000 rpm for 10 min and the plasma was separated and frozen in cryotubes at −20° C. until its analysis.

Chromatographic conditions:

UV detection at 220 nm 10-micron Novapack $C_{18}$ column

Mobile phase: pH 3.5 phosphate buffer/acetonitrile 59:41 V/V

Flow rate: 1.6 ml/min

Internal standard: ibuprofen

Figure 10:
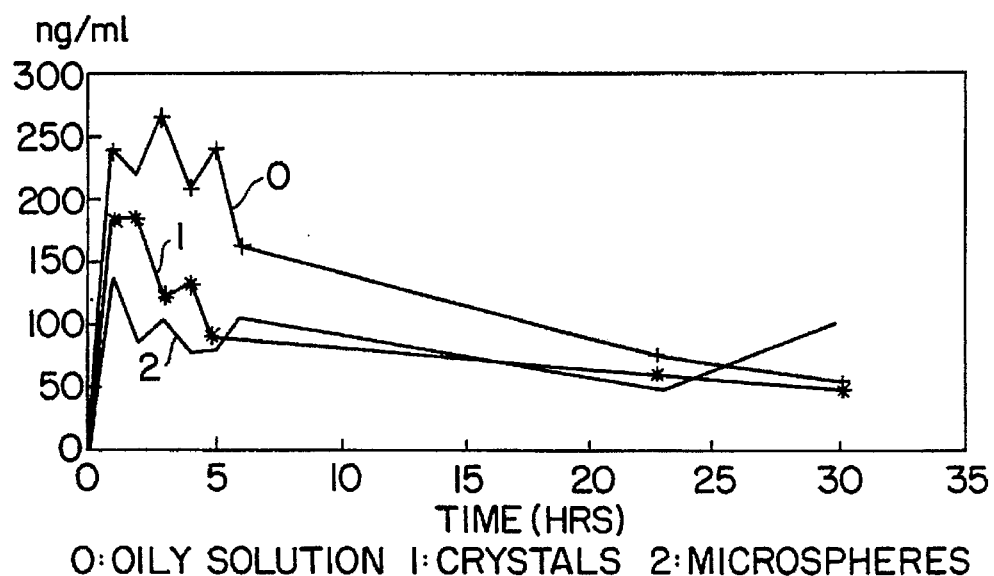
FIG. 10 shows the plasma levels of diazepam obtained in rabbits obtained by an injection of a solution (curve 0) of a suspension of crystals (curve 1) and of microspheres of diazepam/cholesterol (curve 2) respectively.

FIG. 10 shows the evolution of the plasma levels until 30 hours after injection, obtained by injection of respectively an oily solution (curve 0), a suspension of microspheres according formula no 2 of example 8 (curve 2) and a similarly formulated suspension of irregular particles (so-called "crystals"), obtained by mixing cholesterol and diazepam, melting the mixture, refreezing it and crushing it into small particles (curve 1). It can be seen that by means of microspheres, the initial plasma peak is avoided.

In summary, the above disclosed results show that in the initial part of the dissolution process, pharmaceutically active substances exhibit much more reproducible numeric values and much more smoother profiles, in form of batches of calibrated microspheres than in form of random shaped particles. This allows to calculate more accurately a pharmaceutically efficient dose. Moreover, the disappearance of the initial dissolution peak (or at least its dramatic decrease, if compared with crystals or random particles) as well as the delayed and globally extended dissolution process permits to calculate increased unit doses intended to be administered at more spaced periods of time. Furthermore the above disclosed results show that this type of structure may be used as well for the manufacture of drugs whose efficiency-period is relatively short, that is several hours to a few days (for example analgesics), as well as for substances whose intended efficiency-period lasts a few weeks. Among the latter, one may cite in particular the use of sexual hormones (as progesterone or 17-β-estradiol) for the manufacture of a contraceptive intended for monthly parenteral injection or for the manufacture of a post-partum contraceptive, or for the manufacture of a medicinal product for parenteral injection intended for the prevention of ostheoporosis in menopausal women.

The manufacturing process described above, the spherical structures and the formulations obtained and their use by the parenteral route by injection are naturally not limited to the substances given as examples above, but are applicable to all pharmaceutically active substances, chemically stable during the micronisation, on the condition that the pharmaceutical modifications which permit the microspheres (brief or long duration depending on the diameter, regularisation of the plasma profiles) possess a therapeutic advantage or one of convenience and that the doses to be administered do not exceed a reasonable volume. Depending on the intended application, the method of administration may be chosen from among hypodermic injection, subcutaneous injection, intramuscular injection, intra-articular injection, and intra-rachidian injection.

We claim:

1. A pharmaceutical formulation suitable for compounding for parenteral administration to a mammal comprising solid, non-porous microspheres, said microspheres having a diameter of between 5 and 300 μm, wherein said microspheres consist of cholesterol as a carrier substance and particles of a pharmaceutically active substance homogeneously disbursed within said cholesterol carrier substance wherein said microspheres are obtained by spraying said cholesterol in the melted state in which said pharmacologically active substance is either in the dissolved state or in the form of particles less than 5 μm, to form droplets and rapidly freezing said droplets.

2. The pharmaceutical formulation of claim 1, wherein the average diameter of said microspheres is between 10 and 100 μm.

3. The pharmaceutical formulation of claim 2, wherein said microspheres further comprise pharmaceutically active additives.

4. The pharmaceutical formulation of claim 1, wherein said carrier substance is chemically stable when melted, and wherein said pharmaceutically active substance is chemically stable in said carrier substance when said carrier substance is melted.

5. The pharmaceutical formulation of claim 4, wherein said carrier substance is selected from the group consisting of coprosterol, glycocholic acid, cholesterol, and cholesterol esters.

6. The pharmaceutical formulation of claim 1, wherein more than 70% of said microspheres have diameters of between 70% and 130% of a specified diameter, and said specified diameter is between 5 and 300 μm.

7. The pharmaceutical formulation of claim 1 wherein said pharmaceutically active substance comprises a steroidal sexual hormone capable of a contraceptive effect when administered to a mammal.

8. The pharmaceutical formulation of claim 7 wherein the steroidal sexual hormone is selected from among the group consisting of progesterone, testosterone, and 17-β-estradiol.

9. The pharmaceutical formulation of claim 8 wherein the carrier substance is selected from the group consisting of cholesterol and cholesterol esters.

10. The pharmaceutical formulation of claim 1 wherein the active agent is a steroidal medicinal product useful in the prevention of osteoporosis in menopausal women.

11. A method for the manufacture of a pharmaceutical formulation of claim 1 for parenteral administration by injection, comprising the step of combining at least one pharmaceutically active substance with at least one pharmacologically inactive carrier substance into solid, non-porous microspheres wherein the pharmaceutically active substance is homogeneously dispersed within the carrier substance, said microspheres having a diameter of between 5 and 300 μm, wherein said carrier substance is naturally present in mammalian organisms and is stable at temperatures below 60° C., and wherein the kinetics of dissolution of said carrier substance in a mammalian organism into which said microspheres have been injected is slower than the kinetics of release of said active substance in said organism.

12. The method of claim 11, wherein said microspheres are in the form of a powder, and are prepared into a suspension in a pharmaceutically acceptable liquid suspension medium.

13. The method of claim 12, wherein said liquid suspension medium is selected from the group consisting of aqueous solutions.

14. The method of claim 12, wherein said liquid suspension medium is a saline solution.

15. The method of claim 11, wherein said microspheres are combined with a pharmaceutically acceptable liquid suspension medium in which said active substance is at least partially insoluble to form a suspension.

16. The method of claim 11, wherein said active substance is 17-β-estradiol and said carrier substance is cholesterol, and wherein said microspheres act as a contraceptive when administered to an organism in an effective amount.

17. The method of claim 11, further comprising the step of separating said microspheres into calibrated fractions according to particle size, wherein more than 70% of said microspheres have diameters between 70% and 130% of a specified diameter, and said specified diameter is between 5 and 300 μm.

18. The method of claim 12, further comprising the step of separating said microspheres into calibrated fractions according to particle size, wherein more than 70% of said microspheres have diameters between 70% and 130% of a specified diameter, and said specified diameter is between 5 and 300 μm.

19. The method of claim 16, further comprising the step of separating said microspheres into calibrated fractions according to particle size, wherein more than 70% of said microspheres have diameters between 70% and 130% of a specified diameter, and said specified diameter is between 5 and 300 μm.

20. A method for parenteral administration of pharmaceutically active substances, of claim 1, comprising parenteral injection of solid, non-porous microspheres into a mammalian organism, said microspheres comprising at least one pharmaceutically active substance homogeneously dispersed within a pharmacologically inactive carrier substance, said microspheres having a diameter of between 5 and between 300 μm, and wherein said carrier substance is naturally present in said organism and is stable at temperatures below 60° C., and wherein the kinetics of dissolution for said carrier substance in said organism into which said microspheres have been injected is slower than the kinetics of release of said active substance in said organism.

21. The method of claim 20, further comprising the step of separating said microspheres into calibrated fractions according to particle size, wherein more than 70% of said microspheres have diameters between 70% and 130% of a specified diameter, and said specified diameter is between 5 and 300 μm.

* * * * *